US012698293B2

(12) United States Patent
Guo et al.

(10) Patent No.: US 12,698,293 B2
(45) Date of Patent: Aug. 4, 2026

(54) CRYSTAL FORM OF MACROCYCLIC COMPOUND, AND PREPARATION METHOD THEREFOR AND USE THEREOF

(71) Applicant: HITGEN INC., Chengdu (CN)

(72) Inventors: Ruizhi Guo, Guangzhou (CN); Jiansong Wang, Guangzhou (CN); Zhibo Luo, Guangzhou (CN); Haiwen Huang, Guangzhou (CN); Fei Qin, Guangzhou (CN); Wei Wang, Guangzhou (CN); Haihong Ye, Guangzhou (CN); Ribin Qian, Guangzhou (CN)

(73) Assignee: HITGEN INC., Chengdu (CN)

( * ) Notice: Subject to any disclaimer, the term of this patent is extended or adjusted under 35 U.S.C. 154(b) by 321 days.

(21) Appl. No.: 18/694,010

(22) PCT Filed: May 17, 2022

(86) PCT No.: PCT/CN2022/093322
§ 371 (c)(1),
(2) Date: Mar. 21, 2024

(87) PCT Pub. No.: WO2023/045360
PCT Pub. Date: Mar. 30, 2023

(65) Prior Publication Data

US 2024/0287096 A1 Aug. 29, 2024

(30) Foreign Application Priority Data

Sep. 22, 2021 (CN) .......................... 202111111449.1

(51) Int. Cl.
*C07D 498/22* (2006.01)
*A61K 31/4375* (2006.01)

(52) U.S. Cl.
CPC ........ *C07D 498/22* (2013.01); *A61K 31/4375* (2013.01)

(58) Field of Classification Search
CPC .................................................... C07D 498/22
See application file for complete search history.

(56) References Cited

U.S. PATENT DOCUMENTS

| | | | |
|---|---|---|---|
| 2013/0203776 | A1 | 8/2013 | Andrews et al. |
| 2020/0116682 | A1 | 4/2020 | Sasaki |
| 2021/0147443 | A1 | 5/2021 | Li et al. |

FOREIGN PATENT DOCUMENTS

| | | | |
|---|---|---|---|
| CN | 110386945 | A | 10/2019 |
| CN | 112174982 | A | 1/2021 |

(Continued)

OTHER PUBLICATIONS

International Search Report for PCT/CN2022/093322 mailed Aug. 10, 2022, ISA/CN.

(Continued)

*Primary Examiner* — Andrew D Kosar
*Assistant Examiner* — John D Mcanany
(74) *Attorney, Agent, or Firm* — Yue (Robert) Xu; Apex Attorneys at Law, LLP

(57) ABSTRACT

The present invention relates to the technical field of drug synthesis. Disclosed are a crystal form of a macrocyclic compound, and a preparation method therefor and the use thereof. The macrocyclic compound is (6R,16R)-9-fluoro-16-methyl-13-oxa-2,17,21,25-tetraazapentane [16.6.2.$0^{2,6}$.$0^{7,12}$.$0^{22,26}$]dihexadecane-1(25),7,9,11,18(26),19,21,23-octane-19-carbonitrile. The X-ray diffraction pattern of the crystal form has characteristic peaks at 2θ values of 9.49±0.2, 10.60±0.2, 11.54±0.2, 14.10±0.2, 17.09±0.2, 19.15±0.2, 20.30±0.2, 22.85±0.2, 23.89±0.2 and 27.74±0.2.

(Continued)

The crystal form is hygroscopicity-free, has a good stability and pharmacokinetic properties.

10 Claims, 3 Drawing Sheets

(56) References Cited

FOREIGN PATENT DOCUMENTS

| | | | |
|---|---|---|---|
| CN | 113121568 | A | 7/2021 |
| CN | 113754657 | A | 12/2021 |
| JP | 2013530142 | A | 7/2013 |
| JP | 2015112806 | A | 6/2015 |
| JP | 2020001415 | A | 1/2020 |
| JP | 2020063965 | A | 4/2020 |
| JP | 2020094112 | A | 6/2020 |
| JP | 2021517914 | A | 7/2021 |
| JP | 2021115401 | A | 8/2021 |
| WO | 2010085597 | A1 | 7/2010 |

OTHER PUBLICATIONS

Japanese First Office Action issued on Apr. 1, 2025 for the Japanese counterpart application No. 2024-541120.

API Form Screening and Selection in Drug Discovery by Noriyuki Takata, Pharm Stage vol. 6 No. 10 2007,p. 20-25.

Handbook of Organic Compound Crystallization by Noriaki Hirayama, Published on Jul. 25, 2008.

Pharmaceutical Polymorphism and Crystallization Chemistry Published on Sep. 20, 2002.

CRYSTAL FORM OF MACROCYCLIC COMPOUND, AND PREPARATION METHOD THEREFOR AND USE THEREOF

CROSS REFERENCE OF RELATED APPLICATION

The present application is the national phase of International Application No. PCT/CN2022/093322, titled "CRYSTAL FORM OF MACROCYCLIC COMPOUND, AND PREPARATION METHOD THEREFOR AND USE THEREOF", which claims the priority of Chinese Patent Application No. 202111111449.1, filed with the China National Intellectual Property Administration on Sep. 22, 2021, and titled with "CRYSTAL FORM OF MACROCYCLIC COMPOUND, AND PREPARATION METHOD THEREFOR AND USE THEREOF", the entire disclosures thereof are incorporated herein by reference.

FIELD

The present invention relates to the field of drug synthesis, and in particular to a crystal form of a macrocyclic compound, and a preparation method therefor and the use thereof.

BACKGROUND

Tropomyosin-related kinase (abbreviated as Trk kinase) is a class of nerve growth factor receptors. Trk family consists of the highly homologous TrkA, TrkB and TrkC, encoded by the genes NTRK1, NTRK2 and NTRK3, respectively. Under normal physiological conditions, Trk protein is a high-affinity receptor for nerve growth factor. During organogenesis, Trk protein is expressed in neuronal tissues and plays a key role in the development of the central and peripheral nervous systems. NTRK gene fusion caused by chromosomal variation could lead to a high level of chimeric Trk protein expression, resulting in dysregulation of the downstream signaling pathway of Trk kinase. The over-activation of this signaling pathway could lead to cancer.

NTRK gene fusion is presented in a variety of adult and pediatric solid tumors, such as breast cancer, colorectal cancer and non-small cell lung cancer, as well as various sarcomas. Currently, a variety of novel drugs targeting the NTRK fusion gene are in clinical development. These drugs all have an inhibitory activity on Trk kinase, mostly achieving the inhibition of the catalytic activity of the kinase by competing with ATP for binding sites. The prior art discloses a class of macrocyclic kinase inhibitors which shows a good inhibitory activity and selectivity on Trk and good inhibitory effect on tumor growth in vivo. It has been found through studies that, in these compounds, the macrocyclic compound the (6R,16R)-9-fluoro-16-methyl-13-oxa-2,17,21,25-tetraazapentacyclo[16.6.2.$0^{2,6}$.$0^{7,12}$.$0^{22,26}$]hexacosane-1(25), 7,9,11,18(26), 19,21,23-octane-19-carbonitrile has a better effect. The structure of this macrocyclic compound is shown below.

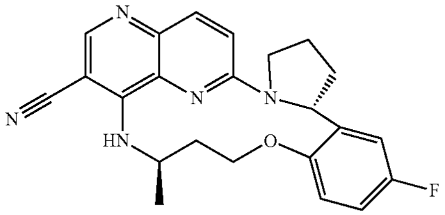 [SMILES: C[C@@H]1CCOc2ccc(F)cc2[C@H]2CCCN2c2ccc3ncc(C#N)c(c3n2)N1]

The prior art discloses a general method for preparing the macrocyclic compound, but does not mention a crystalline form of this compound and a corresponding preparation method therefor.

It is well-known that a drug has polymorphism, i.e., a drug has different crystal forms resulting from different arrangements of drug molecule, which is generally in the solid form of the active pharmaceutical ingredient. A drug may have multiple crystal forms, and the different crystal forms of the same drug may have different stability, dissolution and absorption in the body, thus affecting the clinical efficacy and safety of the drug. There is currently no study on a crystal form of the macrocyclic compound (6R,16R)-9-fluoro-16-methyl-13-oxa-2,17,21,25-tetraazapentacyclo [16.6.2.$0^{2,6}$.$0^{7,12}$.$0^{22,26}$]hexacosane-1(25), 7,9,11,18(26), 19,21,23-octane-19-carbonitrile. The amorphous form of the compound has unfavorable hygroscopicity and stability, thus the resulting drug prepared therefrom does not work well.

Therefore, there is an urgent need to provide a crystal form of the macrocyclic compound, which has good physical and chemical stability, is not hygroscopic, and has good pharmacokinetic properties.

SUMMARY

The present invention aims at solving at least one of the above mentioned technical problems in the prior art. Thus, the present invention provides a crystal form of a macrocyclic compound, which has good physical and chemical stability, is not hygroscopic, and has good pharmacokinetic properties.

In the first aspect of the present invention, provided is a crystal form of a macrocyclic compound.

Specifically, the present invention provides a crystal form of a macrocyclic compound, wherein the macrocyclic compound is (6R,16R)-9-fluoro-16-methyl-13-oxa-2,17,21,25-tetraazapentacyclo [16.6.2.$0^{2,6}$.$0^{7,12}$.$0^{22,26}$]hexacosane-1 (25), 7,9, 11, 18(26), 19,21,23-octane-19-carbonitrile; and the X-ray powder diffraction pattern of the crystal form comprises characteristic peaks at 2θ values of 9.49±0.2, 10.60±0.2, 11.54±0.2, 14.10±0.2, 17.09±0.2, 19.15±0.2, 20.30±0.2, 22.85±0.2, 23.89±0.2 and 27.74±0.2.

Preferably, the X-ray powder diffraction pattern of the crystal form further comprises characteristic peaks at 2θ values of 18.75±0.2, 21.29±0.2, 24.25±0.2, 24.99±0.2, 28.74±0.2 and 31.35±0.2.

Further preferably, the X-ray powder diffraction pattern of the crystal form further comprises characteristic peaks at 2θ values of 5.69±0.2, 16.11±0.2, 25.62±0.2, 26.34±0.2, 27.26±0.2, 29.91±0.2, 32.19±0.2, 33.86±0.2, 34.70±0.2, 35.59±0.2, 36.95±0.2, 37.40±0.2, 39.19±0.2, 40.33±0.2, 41.16±0.2, 42.56±0.2, 43.11±0.2, 45.30±0.2, 46.35±0.2 and 49.80±0.2.

Preferably, the differential scanning calorimetry trace of the crystal form has an endothermic peak at 233±5° C. Further preferably, the differential scanning calorimetry trace of the crystal form has an endothermic peak at 233±3° C.

In the second aspect of the present invention, provided is a method for preparing the crystal form of a macrocyclic compound.

Specifically, the method for preparing the crystal form of a macrocyclic compound is selected form the group consisting of approach (1), adding a solvent to the macrocyclic compound to allow a supersaturation, stirring, precipitating, filtering, obtaining a filter cake, and drying the filter cake to obtain the crystal form;

approach (2), adding the macrocyclic compound to a solvent under heating, then dissolving, cooling, precipitating, filtering, obtaining a filter cake, and drying the filter cake to obtain the crystal form; and approach (3), dissolving the macrocyclic compound in a solvent, adding an anti-solvent, precipitating, filtering, obtaining a filter cake, and drying the filter cake to obtain the crystal form.

In approaches (1)-(3), the macrocyclic compound is (6R, 16R)-9-fluoro-16-methyl-13-oxa-2,17,21,25-tetraazapentacyclo [$16.6.2.0^{2,6}.0^{7,12}.0^{22,26}$]hexacosane-1(25), 7,9,11,18 (26), 19,21,23-octane-19-carbonitrile. The crystalline form of the macrocyclic compound is not specifically limited and other crystal forms and amorphous form may be used.

Preferably, in approach (2), the heating is to a temperature of 40-100° C.; further preferably, in approach (2), the heating is to a temperature of 50-80° C.

Preferably, the solvent in approaches (1)-(3) and the anti-solvent in approach (3) are selected from a group consisting of $C_2$-$C_7$ hydrocarbons, $C_2$-$C_7$ alcohols, $C_2$-$C_7$ ketones, $C_2$-$C_7$ nitriles, $C_2$-$C_7$ ethers, $C_2$-$C_7$ esters, water, and any combination thereof.

Preferably, the $C_2$-$C_7$ hydrocarbons comprise methylene chloride, n-heptane or toluene.

Preferably, the $C_2$-$C_7$ alcohols comprise methanol, ethanol, trifluoroethanol, n-propanol or isopropanol.

Preferably, the $C_2$-$C_7$ ketones comprise acetone or butanone.

Preferably, the $C_2$-$C_7$ nitriles comprise acetonitrile.

Preferably, the $C_2$-$C_7$ ethers comprise isopropyl ether, methyl tert-butyl ether, tetrahydrofuran or 1,4-dioxane.

Preferably, the $C_2$-$C_7$ esters comprise ethyl acetate or isopropyl acetate.

Preferably, the solvent is selected from the group consisting of methanol, ethanol, acetone, dichloromethane, tetrahydrofuran, water, and any combination thereof.

Preferably, the anti-solvent is selected from the group consisting of isopropyl ether, n-heptane and water, or a mixture thereof.

In the third aspect of the present invention, provided is use of the crystal form of the macrocyclic compound.

Specifically, provided is use of the crystal form of the macrocyclic compound in the manufacture of a medicament for treating a Trk kinase-associated disease.

Preferably, the Trk kinase-associated disease is one of pain, a malignant tumor, an inflammatory disease or a neurodegenerative disease.

Preferably, the pain comprises chronic pain and acute pain, including but not limited to, bone pain, visceral pain, inflammatory pain, migraine, chronic low back pain, bladder pain syndrome and neuropathic pain caused by cancer, surgery, fractures, tumor metastases and the like.

Preferably, the malignant tumor refers to any of a wide range of diseases characterized by uncontrolled and abnormal cell proliferation, in which the affected cells are localized or have the ability to spread to other parts of the body through the bloodstream and lymphatic system (i.e., metastasis), and by any of many characteristic structures and/or molecular characteristics. The malignant tumor includes sarcoma, breast cancer, lung cancer, brain cancer, bone cancer, liver cancer, kidney cancer, colon cancer, fibrosarcoma, squamous cell carcinoma, melanoma or ovarian cancer.

Preferably, the inflammatory disease includes various conditions characterized by histopathological inflammation. The inflammatory diseases include acne vulgaris, asthma, celiac disease, chronic prostatitis, glomerulonephritis, inflammatory bowel disease, pelvic inflammatory disease, reperfusion injury, rheumatoid arthritis, sarcoidosis, vasculitis, airway inflammation caused by house dust mites, and interstitial cystitis. There is a significant overlap between inflammatory diseases and autoimmune diseases.

Preferably, the neurodegenerative disease includes multiple sclerosis, Parkinson's disease and Alzheimer's disease.

Compared with the prior art, the present invention has the following advantageous effects.

The crystal form of a macrocyclic compound provided by the present invention is not hygroscopic. High temperature, high humidity or light have little effect on its purity. The crystal form has good chemical stability. This crystal form is unchanged after 6 months of accelerated storage at a temperature of 40±2° C. and a relative humidity of 75±5%, showing good physical stability. Also, this crystal form has good pharmacokinetic properties.

DETAILED DESCRIPTION

In order to make those skilled in the art understand the technical solutions of the present disclosure more clearly, the following examples are given for illustration. It should be noted that the following examples do not limit the protection scope of the present disclosure.

The raw materials and reagents employed in the following examples or comparative example unless otherwise specified, are commercially available or can be obtained by using known methods. The main instruments used in the following examples or comparative example are shown in Table 1.

TABLE 1

| Instrument | Model |
|---|---|
| X-ray Powder Diffractometer (XRPD) | Bruker D8 Advance Diffractometer |
| Differential Scanning Calorimeter (DSC) | TA Instruments Q200 DSC |
| Thermogravimetric Analyzer (TGA) | TA Instruments Q500 TGA |
| Dynamic Vapor Sorption (DVS) | TA Instruments Q5000 TGA |
| High Performance Liquid Chromatography (HPLC) | Agilent 1260 HPLC |

EXAMPLES

Example 1

A method of preparing the crystal form of the macrocyclic compound comprises the following steps.

1 mg of macrocyclic compound the (6R,16R)-9-fluoro-16-methyl-13-oxa-2,17,21,25-tetraazapentacyclo [16.6.2.$0^{2,6}$.$0^{7,12}$.$0^{22,26}$]hexacosane-1(25),7,9,11,18(26), 19,21,23-octane-19-carbonitrile prepared according to example 1 of Patent CN110386945A was added to 1.0 mL of methanol and stirred at room temperature (25±5° C.) to obtain a clear solution after dissolution, and 0.8 mL of water was slowly added dropwise. After a solid was precipitated, this mixture was stirred for a certain time, filtered, and the filter cake was dried to obtain a crystalline powder.

Figure 1:
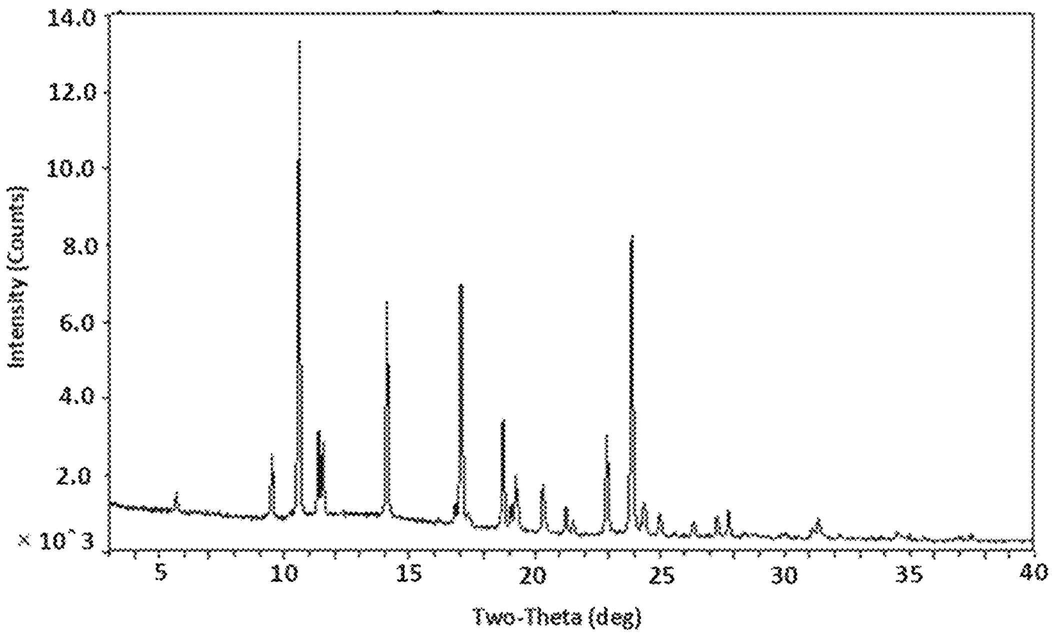
FIG. 1 is the XRPD pattern of the crystal form prepared in example 1 of the present invention.
Figure 2:
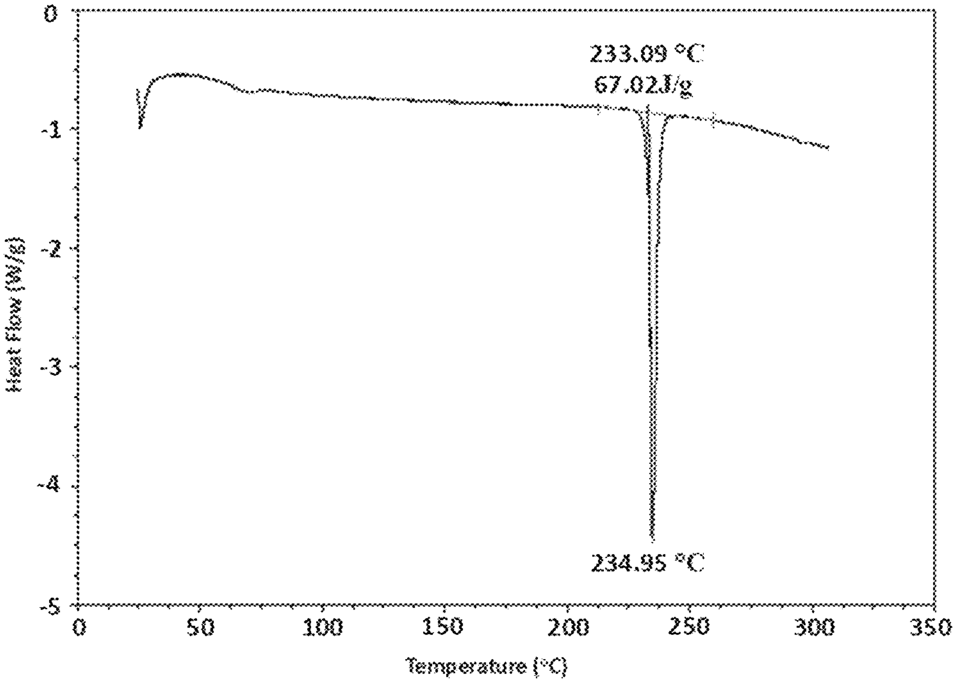
FIG. 2 is the DSC trace of the crystal form prepared in example 1 of the present invention.
Figure 3:
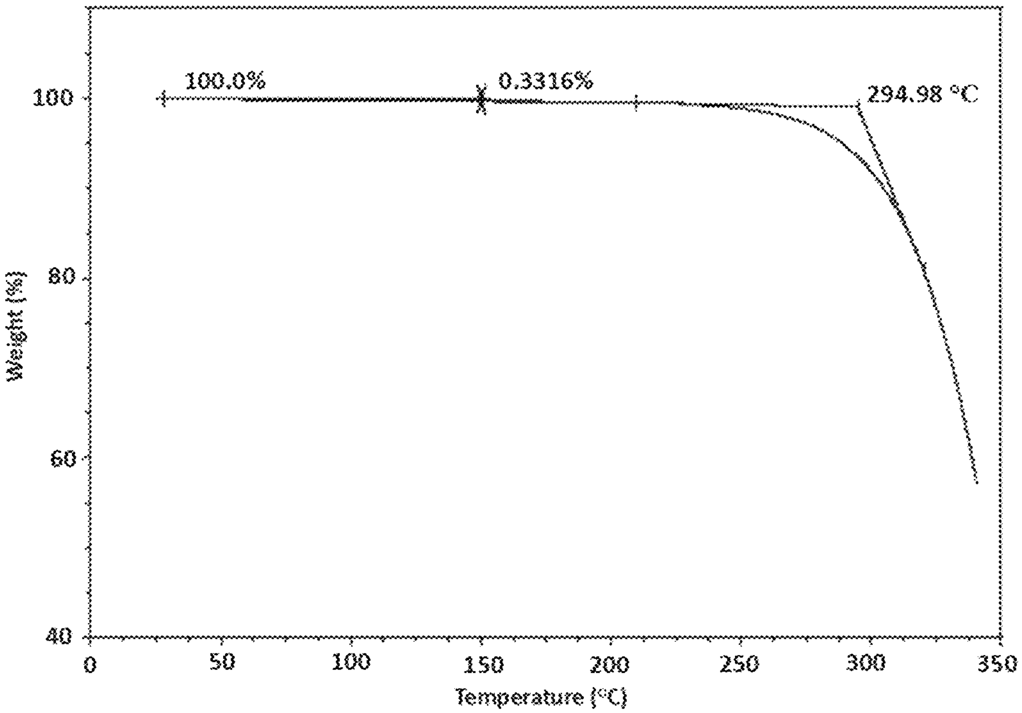
FIG. 3 is the TGA profile of the crystal form prepared in example 1 of the present invention.

The crystalline powder obtained was analyzed by X-ray powder diffraction, differential scanning calorimetry and thermogravimetric analysis. This crystalline sample was characterized and identified as a crystal form. Its XRPD (X-ray powder diffraction) pattern is shown in FIG. 1, showing that this sample has characteristic peaks at 2θ values of 5.69, 9.49, 10.60, 11.54, 14.10, 16.11, 17.09, 18.75, 19.15, 20.30, 21.29, 22.85, 23.89, 24.25, 24.99, 25.62, 26.34, 27.26, 27.74, 28.74, 29.91, 31.35, 32.19, 33.86, 34.70, 35.59, 36.95, 37.40, 39.19, 40.33, 41.16, 42.56, 43.11, 45.30, 46.35 and 49.80, wherein the instrumental error of 20 angle value is ±0.2. The DSC (Differential Scanning calorimetry) trace is shown in FIG. 2, wherein the abscissa is temperature and the ordinate is heat flow, showing that this sample has an endothermic peak at 233° C. The TGA (ThermoGravimetry analysis) profile is shown in FIG. 3, wherein the abscissa is temperature and the ordinate is weight, showing that this sample has a slow weight loss of about 0.3% before 150° C., is anhydrous, and decomposes at about 295° C.

Example 2

A method of preparing the crystal form of the macrocyclic compound comprises the following steps.

15 mg of (6R,16R)-9-fluoro-16-methyl-13-oxa-2,17,21,25-tetraazapentacyclo [16.6.2.$0^{2,6}$.$0^{7,12}$.$0^{22,26}$]hexacosane-1(25), 7,9,11, 18(26), 19,21,23-octane-19-carbonitrile was added to 0.4 mL of methanol and stirred at room temperature to obtain a clear solution after dissolution, and this solution was slowly added to 0.8 mL of water. After a solid was precipitated, the mixture was stirred for a certain time, filtered, and dried to obtain a crystalline pale yellow powder. This crystalline sample was determined to be of the same crystal form as that in Example 1 by comparing of the XRPD pattern and the DSC trace.

Example 3

A method of preparing the crystal form of the macrocyclic compound comprises the following steps.

15 mg of (6R,16R)-9-fluoro-16-methyl-13-oxa-2,17,21,25-tetraazapentacyclo [16.6.2.$0^{2,6}$.$0^{7,12}$.$0^{22,26}$]hexacosane-1(25), 7,9, 11, 18(26), 19,21,23-octane-19-carbonitrile was added to 0.2 mL of dichloromethane and stirred at room temperature to obtain a clear solution after dissolution, and 3.6 mL of n-heptane was slowly added dropwise. After a solid was precipitated, the mixture was stirred for a certain time, filtered, and dried to obtain a crystalline powder. This crystalline sample was determined to be of the same crystal form as that in Example 1 by comparing of the XRPD pattern and the DSC trace.

Example 4

A method of preparing the crystal form of the macrocyclic compound comprises the following steps.

15 mg of (6R,16R)-9-fluoro-16-methyl-13-oxa-2,17,21,25-tetraazapentacyclo [16.6.2.$0^{2,6}$.$0^{7,12}$.$0^{22,26}$]hexacosane-1(25), 7,9,11, 18(26), 19,21,23-octane-19-carbonitrile was added to a mixed solvent of methanol (1.8 mL) and water (0.2 mL), heated to 65° C., stirred to obtain a clear solution after dissolution, slowly cooled and stirred at a holding temperature of 4° C. After a solid was precipitated, this mixture was filtered, and dried to obtain a crystalline powder. This crystalline sample was determined to be of the same crystal form as that in Example 1 by comparing of the XRPD pattern and the DSC trace.

Comparative Example 1

An amorphous form of the macrocyclic compound was prepared as follows.

Figure 4:
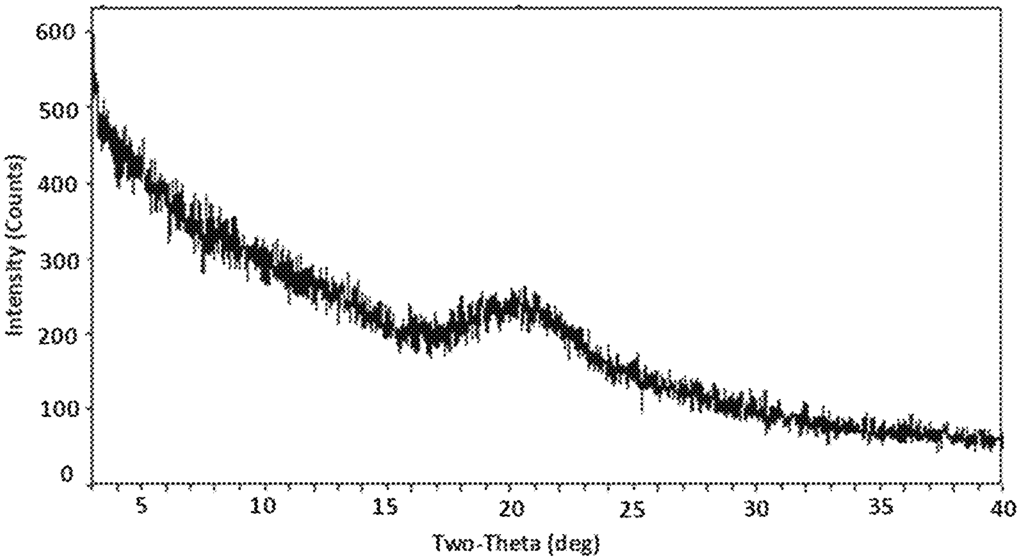
FIG. 4 is the XRPD pattern of the amorphous form prepared in comparative example 1 of the present invention.

15 mg of the compound (6R,16R)-9-fluoro-16-methyl-13-oxa-2,17,21,25-tetraazapentacyclo [16.6.2.$0^{2,6}$.$0^{7,12}$.$0^{22,26}$]hexacosane-1(25),7,9,11,18(26), 19,21,23-octane-19-carbonitrile prepared according to the method disclosed in Patent CN110386945A was added to 0.4 mL of dimethylsulfoxide and stirred at room temperature to obtain a clear solution after dissolution, and 0.6 mL of water was slowly added dropwise. After a solid was precipitated, this mixture was stirred for a certain time, filtered, and dried to obtain a crystalline powder. The crystalline powder obtained was analyzed by X-ray powder diffraction, differential scanning calorimetry and thermogravimetric analysis. This crystalline sample was characterized by X-ray powder diffraction and identified as an amorphous form. The XRPD (X-ray powder diffraction) pattern is shown in FIG. 4, wherein the abscissa is 20 (Two-theta) value and the ordinate is intensity.

Property Test (1) Hygroscopicity Test

The crystal form and amorphous form of the macrocyclic compound provided by the present invention were evaluated for hygroscopicity, and the test was performed using a dynamic vapor sorption to obtain data. The description of the hygroscopicity characteristic and the definition of the weight gain due to hygroscopicity (as shown in Table 2) are referred to China Pharmacopoeia (2020 edition) Part Four General Principles 9103.

TABLE 2

| description of hygroscopicity characteristic | weight gain due to hygroscopicity |
|---|---|
| deliquescence | sufficient water absorbed to form a liquid |
| very hygroscopic | not less than 15% |
| hygroscopic | less than 15% but not less than 2% |
| slightly hygroscopic | less than 2% but not less than 0.2% |
| not or nearly not hygroscopic | less than 0.2% |

Figure 5:
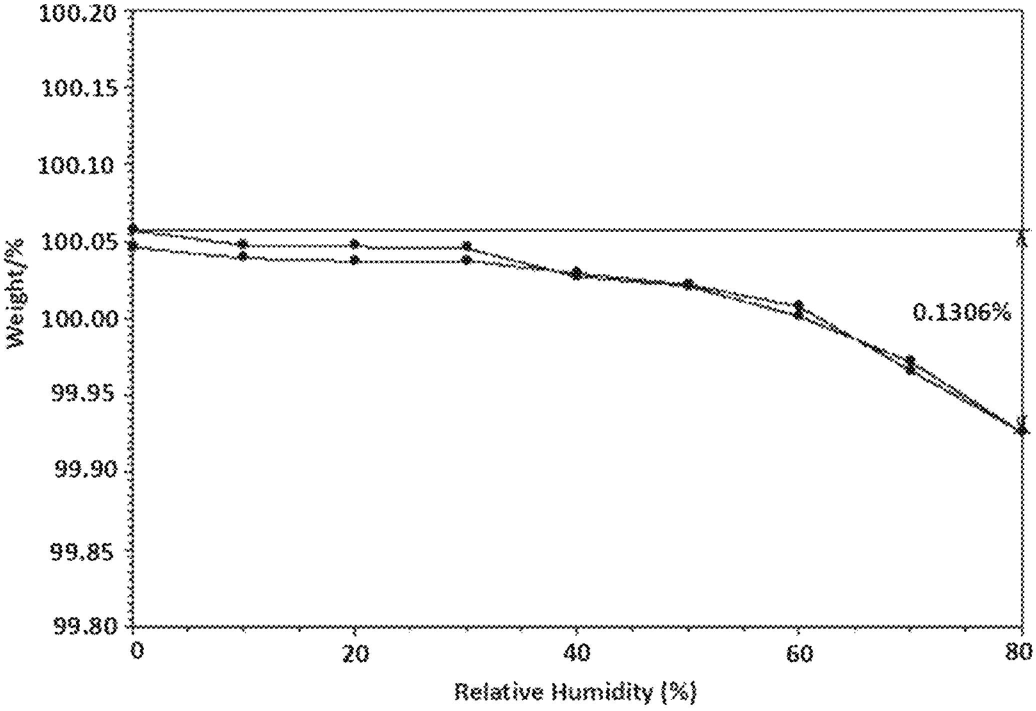
FIG. 5 is the DVS adsorption-desorption isotherm of the crystal form prepared in example 1 of the present invention.
Figure 6:
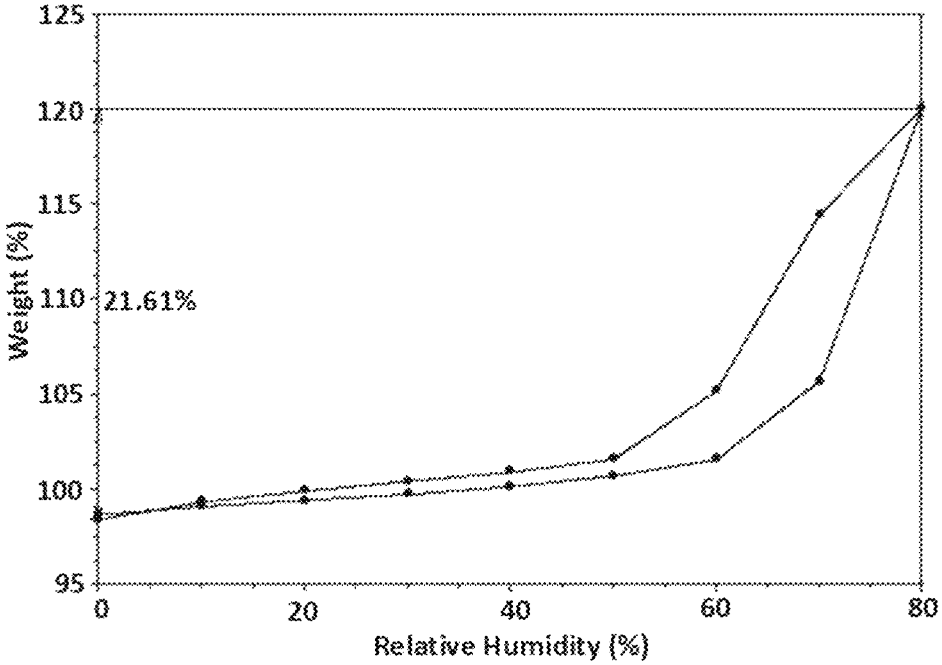
FIG. 6 is the DVS adsorption-desorption isotherm of the amorphous form prepared in comparative example 1 of the present invention.

The adsorption-desorption isotherm of the crystal form prepared in example 1 is shown in FIG. 5, wherein the abscissa is relative humidity and the ordinate is weight (%). The two curves in FIG. 5 represent the adsorption isotherm and desorption isotherm respectively, which do not overlap due to the possibility of desorption hysteresis. FIG. 5 shows that the weight change of the sample was approximately 0.1% with increasing humidity between 0-80% relative humidity, indicating that the sample was not hygroscopic. The adsorption-desorption isotherm of the crystal form prepared in comparative example 1 is shown in FIG. 6, wherein the abscissa is relative humidity and the ordinate is weight (%). The two curves in FIG. 6 represent the adsorption isotherm and desorption isotherm respectively, which do not overlap due to the possibility of desorption hysteresis. FIG. 6 shows that the increase in weight of the sample was about 21.6% with increasing humidity between 0-80% relative humidity, indicating that the sample was very hygroscopic. The experimental results show that this crystal form is better than the amorphous form in terms of hygroscopicity.

(2) Stability Test on Influence Factors

The crystal form and the amorphous form of the macrocyclic compound provided by the present invention were subjected to the stability test on influence factors according to China Pharmacopoeia (2020 edition) Part Four General Principles 9103. Specifically, the crystal form of a macrocyclic compound prepared in example 1 and the amorphous form of the macrocyclic compound prepared in comparative example 1 were placed in an open space under the respective conditions of high temperature (60±2° C.), high humidity (90%±5% RH, 25±2° C.) and light (4500±500 Lx) for 30 days to test stability. The observation period was 30 days. The tested samples were taken on days 5, 10 and 30, and analyzed for purity by high performance liquid chromatography. The data were calculated by area normalization, and the results are shown in Table 3.

TABLE 3

| Condition | Day | Sample purity (%) the crystal form prepared in example 1 | the crystal form prepared in comparative example 1 |
|---|---|---|---|
| — | 0 | 98.8 | 98.1 |
| High temperature, open | 5 | 99.0 | 97.6 |
| High humidity, open | | 98.8 | 97.9 |
| Light, open | | 98.9 | 97.4 |
| High temperature, open | 10 | 98.9 | 97.1 |
| High humidity, open | | 98.8 | 98.0 |
| Light, open | | 98.8 | 96.8 |
| High temperature, open | 30 | 98.9 | 96.9 |
| High humidity, open | | 98.8 | 97.7 |
| Light, open | | 98.6 | 96.4 |

It was shown that the amorphous form of the macrocyclic compound prepared in comparative example 1 showed a decrease in purity under high temperature, high humidity and light conditions during the experimental period, and in particular on day 30, the high temperature and light caused a significant decrease in the purity of the compound. In contrast, the impurity content of the crystal form prepared in example 1 increased slightly under the light condition only and did not change significantly under other conditions.

(3) Accelerated Stability Test

The crystal form of the macrocyclic compound provided by the present invention was subjected to accelerated stability test to examine stability according to China Pharmacopoeia (2020 edition) Part Four General Principles 9103. Specifically, the crystal form was placed in a sealed space at temperature of 40±2° C. and a relative humidity of 75±5% for 6 months. The sample to be tested was taken at months 1, 2, 3 and 6, and detected using X-ray Powder Diffractometer. The results are shown in Table 4.

TABLE 4

| Condition | Observation time (month) | Example 1 |
|---|---|---|
| Temperature (40 ± 2° C.), relative humidity (75 ± 5%), seal | 0 | Initial crystal form |
| | 1 | Same as initial crystal form |
| | 2 | Same as initial crystal form |
| | 3 | Same as initial crystal form |
| | 6 | Same as initial crystal form |

The experiment showed that the crystal form of the macrocyclic compound provided by the present invention remained unchanged during 6 months of testing under accelerated conditions, indicating a better physical stability of the crystal form of the macrocyclic compound provided by the present invention.

(4) Pharmacokinetic Test

After grouped (3 Beagle dogs per group), male beagle dogs were orally administered with the crystal form of the macrocyclic compound provided by the present invention via single gavage at a dose of 8 mg/kg. The plasma was collected at 0.25 h, 0.5 h, 1.0 h, 2.0 h, 4.0 h, 6.0 h, 8.0 h, and 24 h after the administration. A standard curve with appropriate range was established based on the concentration of the tested sample to calculate the concentration of the tested sample in plasma. The quantitative analysis was carried out and the pharmacokinetic parameters were calculated for the tested sample. The results are shown in Table 5, wherein $C_{max}$ represents the peak concentration, $AUC_{0\text{-}last}$ represents the area below the drug-time curve, $T_{max}$ represents peak time of the drug and $T_{1/2}$ represents the half-life of the drug.

TABLE 5

| Tested sample | $T_{max}$ (hour) | $T_{1/2}$ (hour) | $C_0/C_{max}$ (ng/mL) | $AUC_{0\text{-}last}$ (h · ng/mL) |
|---|---|---|---|---|
| Example 1 | 1.3 ± 0.58 | 19 ± 3.9 | 729 ± 208 | 5340 ± 1070 |

As can be seen from Table 5, the crystal form of the macrocyclic compound provided by the present invention is rapidly absorbed in beagle dog and has a great plasma exposure, indicating that it has good pharmacokinetic properties.

The invention claimed is:

1. A crystal form of a macrocyclic compound (6R,16R)-9-fluoro-16-methyl-13-oxa-2,17,21,25-tetraazapentacyclo [16.6.2.0$^{2,6}$.0$^{7,12}$.0$^{22,26}$] hexacosane-1(25),7,9,11,18(26), 19,21,23-octane-19-carbonitrile, wherein the X-ray powder diffraction pattern of the crystal form comprises characteristic peaks at 2θ values of 9.49±0.2, 10.60±0.2, 11.54±0.2, 14.10±0.2, 17.09±0.2, 19.15±0.2, 20.30±0.2, 22.85±0.2, 23.89±0.2 and 27.74±0.2.

2. The crystal form of a macrocyclic compound according to claim 1, wherein the X-ray powder diffraction pattern of the crystal form further comprises characteristic peaks at 2θ values of 18.75±0.2, 21.29±0.2, 24.25±0.2, 24.99±0.2, 28.74±0.2 and 31.35±0.2.

3. The crystal form according to claim 1, wherein the X-ray powder diffraction pattern of the crystal form further comprises characteristic peaks at 2θ values of 5.69±0.2, 16.11±0.2, 25.62±0.2, 26.34±0.2, 27.26±0.2, 29.91±0.2, 32.19±0.2, 33.86-0.2, 34.70±0.2, 35.59±0.2, 36.95±0.2, 37.40±0.2, 39.19±0.2, 40.33±0.2, 41.16±0.2, 42.56±0.2, 43.11±0.2, 45.30±0.2, 46.35±0.2 and 49.80±0.2.

4. The crystal form of a macrocyclic compound according to claim 1, wherein the differential scanning calorimetry trace of the crystal form has an endothermic peak at 233±5° C.

5. A method for preparing the crystal form of a macrocyclic compound according to claim 1, wherein the method is selected form the group consisting of approach (1), approach (2) and approach (3); the approach (1) comprises adding a solvent to the macrocyclic compound to allow for supersaturation, stirring, precipitating, filtering, obtaining a filter cake, and drying the filter cake to obtain the crystal form; the approach (2) comprises adding the macrocyclic compound to a solvent under heating, then dissolving, cooling, precipitating, filtering, obtaining a filter cake, and drying the filter cake to obtain the crystal form; and the approach (3) comprises dissolving the macrocyclic compound in a solvent, adding an anti-solvent, precipitating, filtering, obtaining a filter cake, and drying the filter cake to obtain the crystal form.

6. The method according to claim 5, wherein the solvent in approaches (1)-(3) and the anti-solvent in approach (3) are selected from the group consisting of $C_2$-$C_7$ hydrocarbons, $C_2$-$C_7$ alcohols, $C_2$-$C_7$ ketones, $C_2$-$C_7$ nitriles, $C_2$-$C_7$ ethers, $C_2$-$C_7$ esters, water, and any combination thereof.

7. The method according to claim 6, wherein the $C_2$-$C_7$ hydrocarbons comprise dichloromethane, n-heptane or toluene, the $C_2$-$C_7$ alcohols comprise methanol, ethanol, trifluoroethanol, n-propanol or isopropanol, the $C_2$-$C_7$ ketones comprise acetone or butanone, the $C_2$-$C_7$ nitriles comprise acetonitrile, the $C_2$-$C_7$ ethers comprise isopropyl ether, methyl tert-butyl ether, tetrahydrofuran or 1,4-dioxane, and the $C_2$-$C_7$ esters comprise ethyl acetate or isopropyl acetate.

8. The method according to claim 6, wherein the solvent is selected from the group consisting of methanol, ethanol, acetone, dichloromethane, tetrahydrofuran, water, and any combination thereof, and the anti-solvent is selected from the group consisting of isopropyl ether, n-heptane, water, and any combination thereof.

9. A method of treating a Trk kinase-associated disease, comprising administering the crystal form of a macrocyclic compound according to claim 1 to a subject in need thereof.

10. The method according to claim 9, wherein the Trk kinase-associated disease is any one of the group consisting of pain, a malignant tumor, an inflammatory disease and a neurodegenerative disease, wherein each of these diseases is a Trk kinase-associated form of the disease.

* * * * *